US008754843B2

(12) United States Patent
Abe (10) Patent No.: US 8,754,843 B2
(45) Date of Patent: Jun. 17, 2014

(54) ELECTROPHORETIC DEVICE, METHOD FOR DRIVING SAME, AND ELECTRONIC APPARATUS

(75) Inventor: Daisuke Abe, Chino (JP)

(73) Assignee: Seiko Epson Corporation, Tokyo (JP)

( * ) Notice: Subject to any disclaimer, the term of this patent is extended or adjusted under 35 U.S.C. 154(b) by 1044 days.

(21) Appl. No.: 12/397,965

(22) Filed: Mar. 4, 2009

(65) Prior Publication Data

US 2009/0223821 A1  Sep. 10, 2009

(30) Foreign Application Priority Data

Mar. 5, 2008 (JP) .................................. 2008-055362
Jan. 26, 2009 (JP) .................................. 2009-014452

(51) Int. Cl.
*G09G 3/34* (2006.01)
(52) U.S. Cl.
USPC ......................................................... 345/107
(58) Field of Classification Search
USPC ......................................................... 345/107
See application file for complete search history.

(56) References Cited

U.S. PATENT DOCUMENTS

| 6,323,989 | B1 * | 11/2001 | Jacobson et al. | 359/296 |
| 7,206,119 | B2 * | 4/2007 | Honeyman et al. | 359/296 |
| 2003/0117016 | A1 * | 6/2003 | Ukigaya | 305/107 |
| 2004/0246562 | A1 * | 12/2004 | Chung et al. | 359/296 |
| 2005/0179641 | A1 * | 8/2005 | Zhou et al. | 345/107 |
| 2006/0170648 | A1 * | 8/2006 | Zhou et al. | 345/107 |
| 2006/0192751 | A1 | 8/2006 | Miyasaka et al. | |
| 2006/0198422 | A1 * | 9/2006 | Chopra et al. | 374/158 |
| 2007/0046623 | A1 * | 3/2007 | Song | 345/107 |
| 2007/0247417 | A1 | 10/2007 | Miyazaki et al. | |
| 2007/0296690 | A1 * | 12/2007 | Nagasaki | 345/107 |
| 2010/0265245 | A1 | 10/2010 | Miyasaka et al. | |
| 2012/0062619 | A1 | 3/2012 | Miyasaka et al. | |

FOREIGN PATENT DOCUMENTS

| JP | A-2000-194020 | 7/2000 |
| JP | A-2002-014654 | 1/2002 |
| JP | A-2002-116733 | 4/2002 |
| JP | A-2004-163567 | 6/2004 |
| JP | A-2005-501296 | 1/2005 |
| JP | A-2006-267982 | 10/2006 |
| JP | A-2007-213014 | 8/2007 |
| JP | A-2007-316594 | 12/2007 |

OTHER PUBLICATIONS

Machine translation to English of Japanese patent publication No. 2004-163567, published Jun. 10, 2004.*

* cited by examiner

*Primary Examiner* — Quan-Zhen Wang
*Assistant Examiner* — David Lee
(74) *Attorney, Agent, or Firm* — Oliff PLC (57) ABSTRACT

An electrophoretic device includes: an electrophoretic layer including a plurality of first particles having a relatively high mobility and charged with negative electricity and a plurality of second particles having a relatively low mobility and charged with positive electricity; a first electrode and a second electrode facing each other via the electrophoretic layer; and a control unit applying a first voltage between the first and the second electrodes to control such that the first electrode is at a higher potential than the second electrode and applying a pulse-form second voltage between the first and the second electrodes intermittently a plurality of number of times to control such that the first electrode is at a lower potential than the second electrode, each second voltage applied by the control unit the plurality of number of times having an approximately same pulse width and an approximately same voltage value, as well as the number of times of application of the second voltage being determined based on a desired gradation.

10 Claims, 7 Drawing Sheets

ELECTROPHORETIC DEVICE, METHOD FOR DRIVING SAME, AND ELECTRONIC APPARATUS

The entire disclosure of Japanese Patent Application Nos: 2008-055362, filed Mar. 5, 2008 and 2009-014452, filed Jan. 26, 2009 are expressly incorporated by reference herein.

BACKGROUND

1. Technical Field

The present invention relates to an electrophoretic device with an electrophoretic layer that includes electrophoretic particles (a dispersion system), a method for driving the electrophoretic device, and an electronic apparatus incorporating the electrophoretic device.

2. Related Art

Conventionally, as a method for controlling gradation in an electrophoretic device, there is known a technique of applying a pulse-form voltage by adjusting a pulse length (see JP-A-2002-116733, for example). However, the method requires precise control of the length of an extremely short pulse, so that it is difficult to express multiple gradations. In order to solve the difficulty, there is known a method for intentionally providing variation to characteristics of electrophoretic particles. Even in this method, for example, in order to perform control for 10 gradations, a pulse length needs to be controlled with a precision level equal to or less than 1 ms. Additionally, high-precision gradation control cannot be easily accomplished, since changes in environments such as temperature and humidity cause fluctuations of behaviors of electrophoretic particles and characteristics of a control substrate.

SUMMARY

An advantage of the present invention is to provide an electrophoretic device in which gradation control can be easily performed with high precision. Another advantage of the invention is to provide a method for driving the electrophoretic device, and still another advantage of the invention is to provide an electronic apparatus incorporating the electrophoretic device.

An electrophoretic device according to a first aspect of the invention includes: an electrophoretic layer including a plurality of first particles having a relatively high mobility and charged with negative electricity and a plurality of second particles having a relatively low mobility and charged with positive electricity; a first electrode and a second electrode facing each other via the electrophoretic layer; and a control unit applying a first voltage between the first and the second electrodes to control such that the first electrode is at a higher potential than the second electrode and applying a pulse-form second voltage between the first and the second electrodes intermittently a plurality of number of times to control such that the first electrode is at a lower potential than the second electrode, each second voltage applied by the control unit the plurality of number of times having an approximately same pulse width and an approximately same voltage value, as well as the number of times of application of the second voltage being determined based on a desired gradation.

An electrophoretic device according to a second aspect of the invention includes: an electrophoretic layer including a plurality of particles having a relatively high mobility and charged with positive electricity and a plurality of second particles having a relatively low mobility and charged with negative electricity; a first electrode and a second electrode facing each other via the electrophoretic layer; and a control unit applying a first voltage between the first and the second electrodes to control such that the first electrode is at a lower potential than the second electrode and applying a pulse-form second voltage between the first and the second electrodes intermittently a plurality of number of times to control such that the first electrode is at a higher potential than the second electrode, each second voltage applied by the control unit the plurality of number of times having an approximately same pulse width and an approximately same voltage value, as well as the number of times of application of the second voltage being determined based on a desired gradation.

The electrophoretic device of each of the above aspects uses the two kinds of the particles (the electrophoretic particles) having the different mobility provided in the electrophoretic layer. First, the first voltage is applied between the first and the second electrodes to perform an initial setting. Thereafter, the pulse-form second voltage is applied between the electrodes the plurality of number of times. The number of times of application of the second voltage enables gradation control to be accomplished, thereby eliminating need for high-precision pulse length control.

In the electrophoretic device of the first aspect, preferably, the control unit supplies a reference potential to the first electrode and supplies a lower or higher potential than the reference potential to the second electrode to determine the first and the second voltages.

Fixing the potential of the first electrode at the reference potential (e.g. a ground potential) can contribute to simplification of a voltage generating circuit or the like.

In the electrophoretic device of the first aspect, preferably, a display surface of the electrophoretic device is located on a side where the first electrode is arranged. The display surface means a surface where a user visually recognizes images.

In the electrophoretic device of the first aspect, preferably, the first and the second voltages have an equal absolute value.

This can contribute to further simplification of the voltage generating circuit or the like.

A method for driving an electrophoretic device according to a third aspect of the invention, the electrophoretic device includes; a plurality of first particles having a relatively high mobility and charged with negative electricity and a plurality of second particles having a relatively low mobility and charged with positive electricity in an electrophoretic layer; a first electrode and a second electrode to face each other via the electrophoretic layer; and a control unit to control a voltage applied between the first and the second electrodes. The method includes: (a) applying a first voltage between the first and the second electrodes by the control unit to control such that the first electrode is at a higher potential than the second electrode so as to allow the first particles to be distributed near the first electrode; and (b) applying a pulse-form second voltage between the first and the second electrodes by the control unit intermittently a plurality of number of times to control such that the first electrode is at a lower potential than the second electrode so as to allow a part of the first particles distributed near the first electrode to move near the second electrode, each second voltage applied the plurality of number of times at step (b) having an approximately same pulse width and an approximately same voltage value, as well as the number of times of application of the second voltage being determined based on a desired gradation.

A method for driving an electrophoretic device according to a fourth aspect of the invention, the electrophoretic device includes: a plurality of first particles having a relatively high mobility and charged with positive electricity and a plurality of second particles having a relatively low mobility and charged with negative electricity in an electrophoretic layer; a first electrode and a second electrode to face each other via the electrophoretic layer; and a control unit to control a voltage applied between the first and the second electrodes. The method includes: (c) applying a first voltage between the first and the second electrodes by the control unit to control such that the first electrode is at a lower potential than the second electrode so as to allow the first particles to be distributed near the first electrode; and (d) applying a pulse-form second voltage between the first and the second electrodes by the control unit intermittently a plurality of number of times to control such that the first electrode is at a higher potential than the second electrode so as to allow a part of the fast particles distributed near the first electrode to move near the second electrode, each second voltage applied the plurality of number of times at step (d) having an approximately same pulse width and an approximately same voltage value, as well as the number of times of application of the second voltage being determined based on a desired gradation.

The method for driving an electrophoretic device of each of the above aspects uses the two kinds of the particles (the electrophoretic particles) having the different mobility provided in the electrophoretic layer. First, after performing an initial setting by applying the first voltage between the first and the second electrodes, the pulse-form second voltage is applied between the electrodes the plurality of number of times. The number of times of application of the second voltage enables gradation control to be accomplished, thereby eliminating need for high-precision pulse length control.

In the electrophoretic device driving method of the third aspect, preferably, at step (a), the second particles are dispersed and distributed between the first and the second electrodes.

In the electrophoretic device driving method of the third aspect, preferably, the control unit supplies a reference potential to the first electrode and supplies a potential lower or higher than the reference potential to the second electrode to determine the first and the second voltages. Additionally, in the driving method of the third aspect, preferably, the first and the second voltages have an equal absolute value.

This can contribute to further simplification of the voltage generating circuit or the like.

An electronic apparatus according to a fifth aspect of the invention includes the electrophoretic device according to the first aspect. In this case, the electronic apparatus encompasses various kinds of apparatuses including a display showing display images provided by an electrophoretic material, such as display apparatuses, television apparatuses, electronic papers, watches, electronic calculators, mobile phones, and mobile terminal apparatuses. In addition, aside from the concept of "apparatus", for example, there may be mentioned paper-like or film-like flexible objects, products belonging to immobile objects such as a wall surface with the flexible objects attached thereon, and products belonging to mobile objects such as vehicles, aircraft, and ships using the flexible objects.

BRIEF DESCRIPTION OF THE DRAWINGS

The invention will be described with reference to the accompanying drawings, wherein like numbers reference like elements.

FIGS. 1A to 4C are illustrations showing distribution states of electrophoretic particles.

DESCRIPTION OF EXEMPLARY EMBODIMENT

An embodiment of the invention will be described with reference to the drawings.

Figure 1:
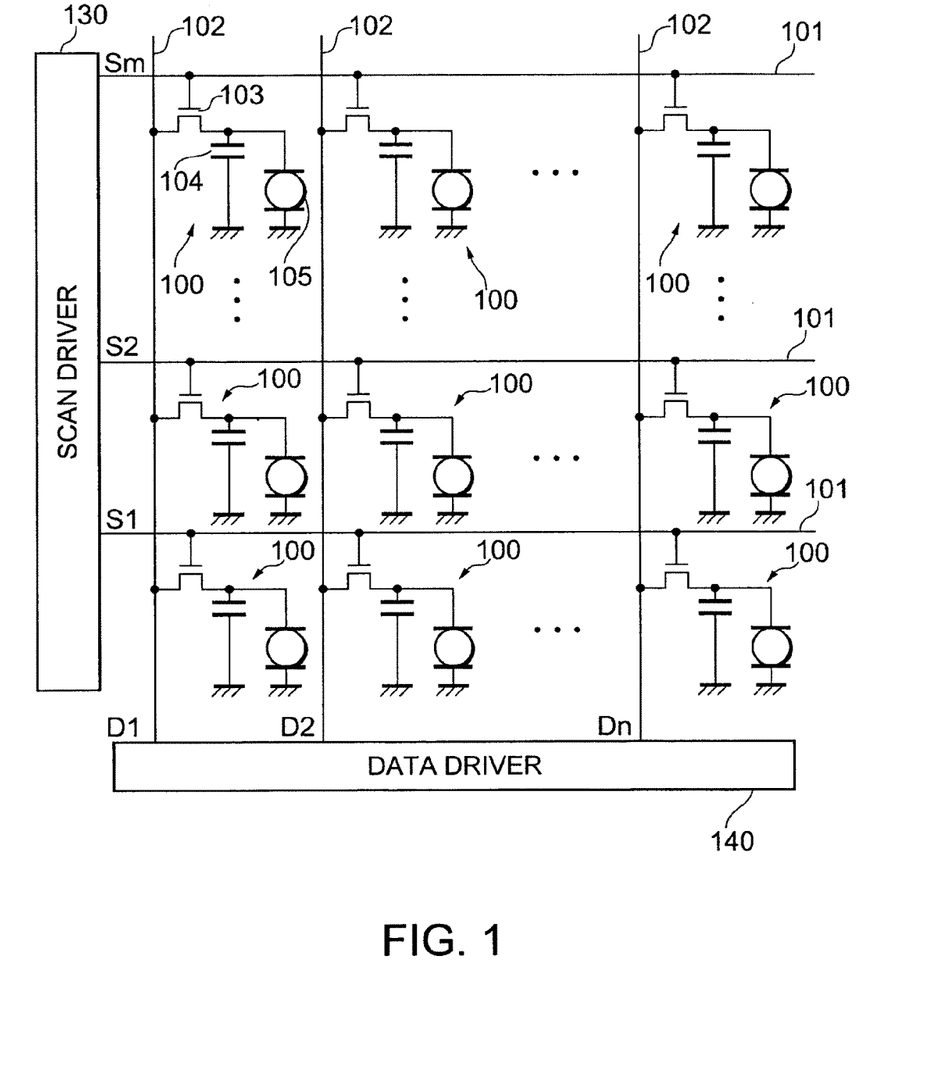
FIG. 1 is a circuit diagram schematically showing a structure of an electrophoretic device

FIG. 1 is a schematic circuit diagram showing a structure of an electrophoretic device according to an embodiment of the invention. The electrophoretic device of the embodiment includes a plurality of pixels 100 arranged in a matrix. Controlling a status of an electrophoretic element 105 included in each pixel 100 allows reflectance of external light in the each pixel 100 to be controlled at multiple gradation levels, thereby forming an externally recognizable image. The structure of the electrophoretic device will be further described with reference FIG. 1. The electrophoretic device of the embodiment further includes a plurality of scan lines 101, a plurality of data lines 102 arranged intersecting with the scan lines 101, a plurality of transistors (switching elements) 103 each arranged at each of intersections between the scan lines 101 and the data lines 102, a plurality of capacitance elements 104 and a plurality of electrophoretic elements, both of which are connected to any one of the transistors 103, a scan driver (a scan-line driving circuit) 130 connected to each of the scan lines 101, and a data driver (a data-line driving circuit) 140 connected to each of the data lines 102. In the present embodiment, the scan driver 130 and the data driver 140 serve as a "control unit".

The each pixel 100 includes each transistor 103, each capacitance element 104, and each electrophoretic element 105. The transistor 103 receives a scan signal from the scan driver 130 via the scan line 101 connected to a gate of the transistor and receives a data signal from the data driver 140 via the data line 102 connected to a source of the transistor. The capacitance element 104 has a first terminal connected to a drain of the transistor 103 and a second terminal connected to a reference potential (a ground potential in the embodiment).

The electrophoretic element 105 has an individual electrode as a first terminal connected to the drain of the transistor 103 and a common electrode as a second terminal connected to a reference potential. Next, a structure of each electrophoretic element 105 will be described with reference to FIGS. 4A to 4C. The electrophoretic element 105 includes a common electrode 110, an individual electrode (a pixel electrode) 111, and an electrophoretic layer 112 between the common electrode 110 and the pixel electrode 111. The common electrode 110 is formed across the electrophoretic elements 105 of the pixels 100 to be shared across the elements 105.

Figure 4A:
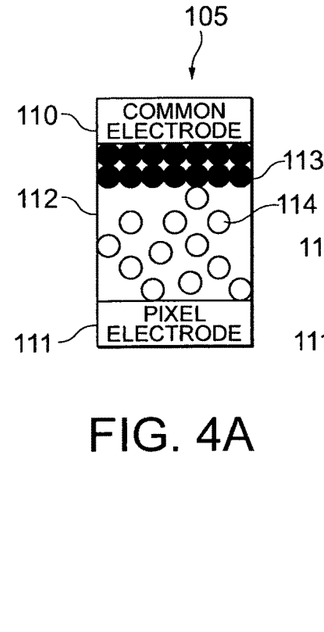
Figures 4B, 4C:
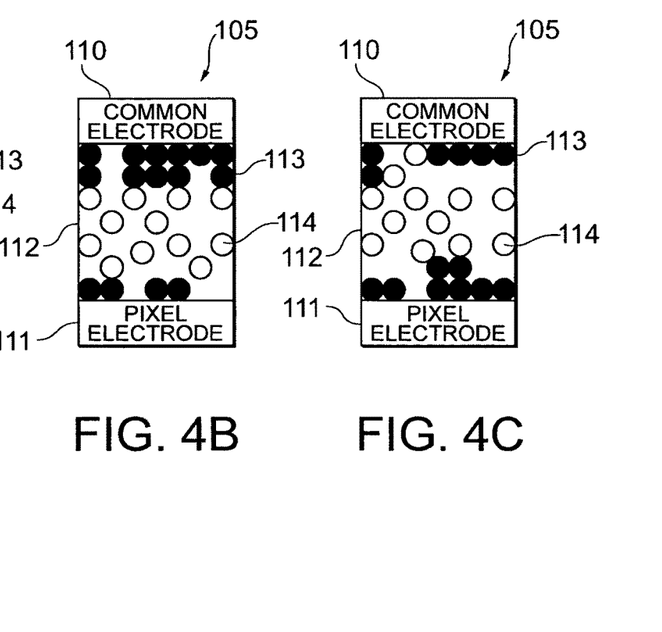

The electrophoretic layer 112 includes a large number of black particles (first particles) 113 and a large number of while particles (second particles) 114 in the layer. In the embodiment, the black and the white particles 113 and 114 have an approximately same size (particle diameter) and have a different amount of charge such that the black particles 113 have mobility three times higher than that of the white particles 114. In short, the mobility of the black particles 113 is higher than the mobility of the white particles 114. Additionally, in the embodiment, the black particles 113 are charged with negative electricity, whereas the white particles 114 are charged with positive electricity. In the electrophoretic device of the embodiment, images are formed such that the images can be recognized from a side adjacent to the common electrode 110. Specifically, white display is performed by applying a voltage allowing the pixel electrode 11 to have a relatively high potential. Conversely, applying a voltage allowing the pixel electrode 111 to have a relatively low potential leads to black display. A dispersion medium, the electrophoretic particles, and the like included in the electrophoretic layer 112 can be obtained by using well-known techniques (for example, see JP-A-2007-213014). Color tones of the particles are arbitrarily determined, and the combination of black and while in the present embodiment is an example among many possible combinations, and thus, other combinations can be considered in embodiment of the invention.

Figure 2:
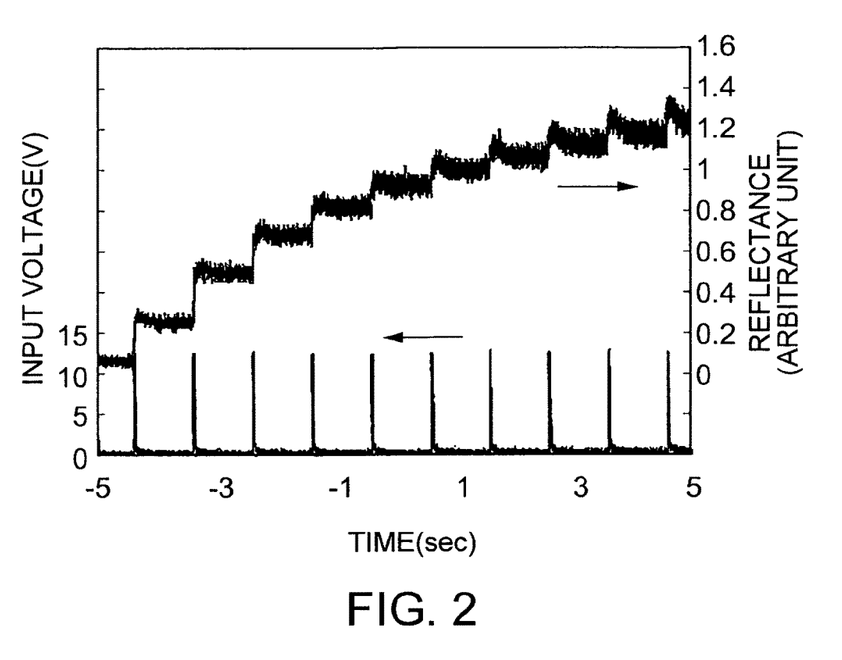
FIG. 2 is a waveform chart illustrating a driving mechanism of an electrophoretic element.
Figure 3:
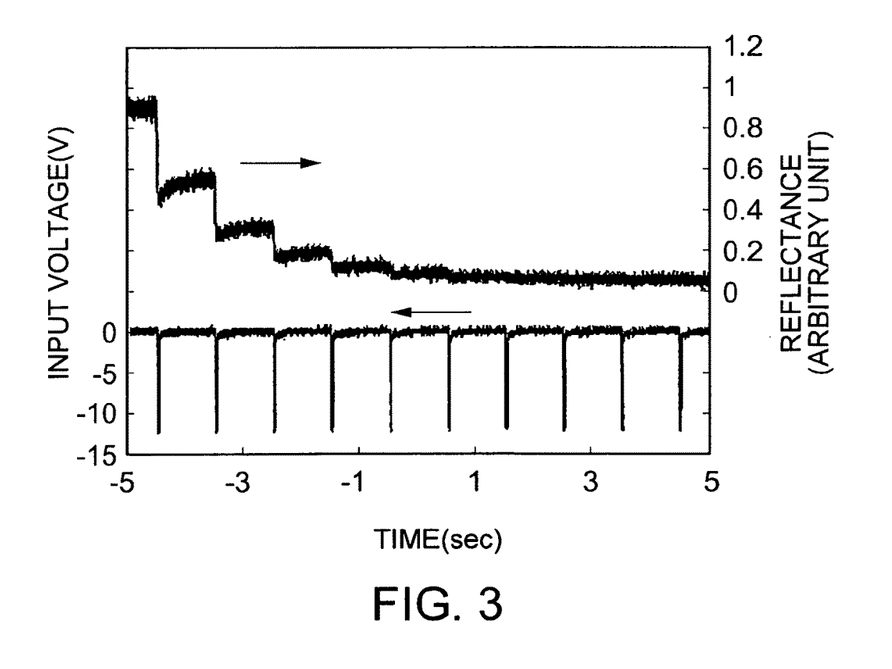
FIG. 3 is another waveform chart illustrating the driving mechanism of the electrophoretic element.

FIGS. 2 and 3 are waveform charts illustrating a driving mechanism of the each electrophoretic element in the embodiment. In each of the drawings, a horizontal axis of the chart represents time durations (unit: second) and a left longitudinal axis thereof represents applied voltages (unit: V), and a right longitudinal axis thereof represents reflectance (an arbitrary unit). A high reflectance status corresponds to white display, and a low reflectance status corresponds to black display. A state in which the pixel electrode 111 has a higher potential than a potential of the common electrode 110 (the reference potential) corresponds to "positive voltage application", whereas vice versa corresponds to "negative voltage application".

FIG. 2 shows reflectance changes observed at the side adjacent to the common electrode 110 when a short pulse with a positive potential (e.g. +12V) is applied a plurality of number of times to the pixel electrode 111 in the electrophoretic element 105 in which the electrophoretic particles are distributed to show a "black display status" (a state in which reflectance is low at the side adjacent to the common electrode 110). Each pulse has a pulse width of 20 ms, and an input interval (a frequency) is 1 Hz. The chart of FIG. 2 shows that applying the positive potential pulse the plurality of number of times in the short interval gradually increases the reflectance according to a total number of times of pulse application. In other words, according to the number of the short pulse applied, gradation can be controlled from the black display to half tones, and then to the white display.

FIG. 3 shows reflectance changes observed at the side adjacent to the common electrode 110 when a short pulse with a negative potential (e.g. −12V) is applied, a plurality of number of times, to the pixel electrode 111 in the electrophoretic element 105 in which the electrophoretic particles are distributed to show a "white display status" (a state in which reflectance is high at the side adjacent to the common electrode 110). Each pulse has the pulse width of 20 ms, and an input interval (a frequency) is 1 Hz. The chart of FIG. 3 shows that applying the positive potential pulse the plurality of number of times in the short interval gradually decreases the reflectance according to the number of times of pulse application. In other words, according to the number of the short pulse applied, gradation can be controlled from the white display to half tones, and then to the black display.

As shown in FIGS. 2 and 3, when the electrophoretic element 105 is driven under conditions of the same pulse width, the same frequency, and the same voltage (the absolute value), the reflectance change with respect to the number of pulses tends to be faster in the gradation control from the white display to the black display (FIG. 3) than in the gradation control from the black display to the white display (FIG. 2). As shown in FIG. 2, when shifting from the black display to the white display, reflectance change per pulse is relatively small. Thus, the gradation control can be performed with high precision depending on the number of times of application of the pulse. Meanwhile, in FIG. 3, reflectance change per pulse is relatively large when shifting from the white display to the black display, and thus, high-precision gradation control cannot be easily performed. Accordingly, in order to control the gradation with higher precision, it is obviously effective to apply a positive potential pulse to the pixel electrode 111 by a predetermined number of times based on a desired gradation (luminescence) after the electrophoretic particles of the each electrophoretic element 105 are initially distributed so as to correspond to the black display status. In addition, even when shifting from the white display to the black display, making the pulse width as short as possible enables the gradation control to be performed with higher precision.

In the embodiment, it is preconditioned that the each electrophoretic element 105 is visually recognized from the side adjacent to the common electrode 110. Conversely, in order to visually recognize the electrophoretic element 105 from a side adjacent to the each pixel electrode 111, the black display status may be pre-set to correspond to visual recognition from the side adjacent to the pixel electrode 111, and thereafter, a negative potential pulse may be applied to the each pixel electrode 111 a plurality of number of times. Thereby, gradation can be expressed under high-precision control.

FIGS. 4A to 4C illustrate examples of a distribution state of the electrophoretic particles. The electrophoretic particles in the electrophoretic device of the embodiment seem to be distributed as follows. FIG. 4A shows a distribution state of the electrophoretic particles observed when the potential of the pixel electrode 111 is lower than the potential of the common electrode 110. In the embodiment, since the black particles 113 have a relatively high mobility and thus is highly responsive to an electric filed, a majority of the black particles 113 gathers near the common electrode 110, whereas the white particles 114 having a relatively low mobility and thus a low responsiveness to the electric field are dispersed broadly in the electrophoretic layer 112. FIG. 4B shows a distribution state of the electrophoretic particles when a positive potential pulse is applied once to the pixel electrode 111. Among the black particles 113 highly responsive to the electric field, some black particles are pulled toward the pixel electrode 111 and moved to a surface of the pixel electrode 111. In this case, due to the short pulse width, not all of the black particles 113 but those near the pixel electrode 111 among the black particles 113 distributed in an overlapping manner are first moved to the surface thereof. FIG. 4C shows a distribution state of the electrophoretic particles when the positive potential pulse is applied to the pixel electrode 111 one more time. With application of the pulse again, a part of the black particles 113 is pulled toward the pixel electrode 111 and moved to the surface of the pixel electrode 111. Also in this case, since the pulse width is short, only the black particles 113 near the pixel electrode 111 among those overlapping each other are first moved to the surface of the pixel electrode 111.

As shown in FIGS. 4A to 4C described above, it is found that since the black particles 113 move faster than the white particles 114, the change from the black display to the white display (the side adjacent to the common electrode 110 in the drawings) is slow, whereas the change from the white display to the black display is fast. In this case, for high-precision gradation control, it is surely better to allow the distribution state of the electrophoretic particles to correspond to the white display status by applying the pulse-form voltage a plurality of times after setting an initial state to the black display status, as compared to vice versa, namely from the white to the black display. This is due to the fact that the mobility of the black particles 113 is higher than that of the white particles 114. Accordingly, when the mobility of the white particles 114 is higher than that of the black particles 113, conversely to the above, the distribution of the electrophoretic particles is initially controlled so as to correspond to the white display status, and then, pulse voltage application is repeated a plurality of number of times such that the distribution state of the electrophoretic particles gradually comes to correspond to the black display status, thereby achieving high-precision gradation control. Hereinafter, the gradation control will be described in detail regarding each of the cases in which the mobility of the black particles 113 is higher than that of the white particles 114 and vice versa.

Figure 5:
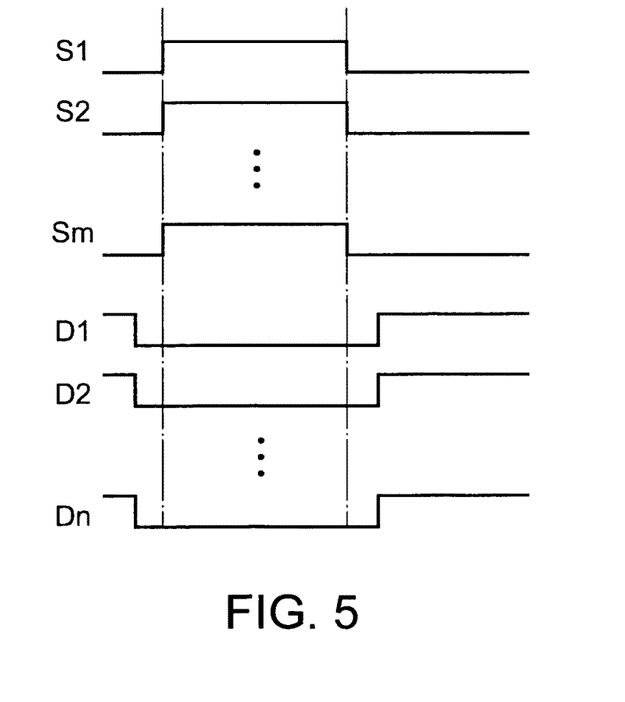
FIG. 5 is a timing chart illustrating an example of gradation control in the electrophoretic device.
Figure 6:
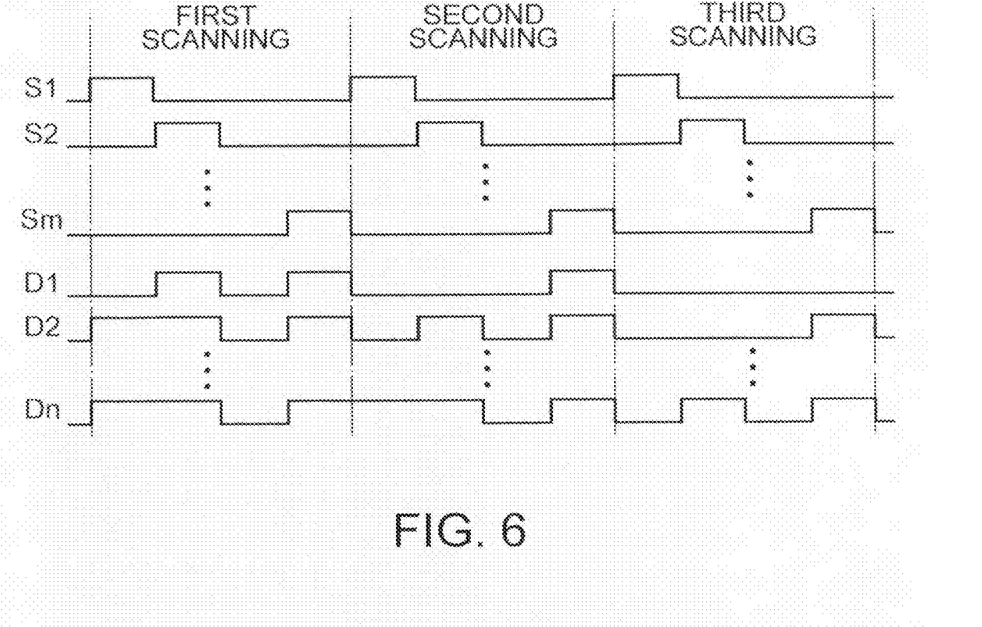
FIG. 6 is a timing chart illustrating the example of gradation control in the electrophoretic device.
Figure 7A:
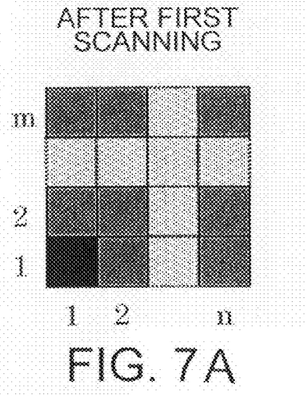
FIGS. 7A to 7C are diagrams schematically showing an example of gradation changes in the electrophoretic particles corresponding to the timing charts shown in FIGS. 5 and 6.
Figure 7B:
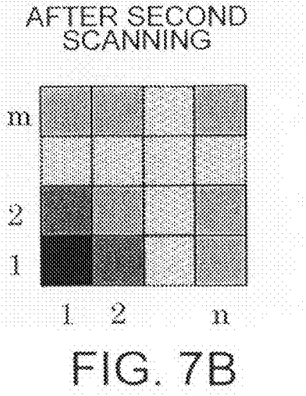
Figure 7C:
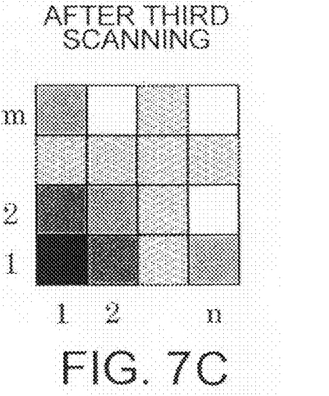

FIGS. 5 and 6 are timing charts illustrating an example of the gradation control in the electrophoretic device according to the embodiment. In the example, the mobility of the black particles 113 is higher than that of the white particles 114. The charts of the drawings correspond to the electrophoretic element 105 arranged in an m-th row and an n-th column in FIG. 1 shown above. In the charts, symbols S1, S2 to Sm represent scan signals supplied to the scan lines 101, and symbols D1, D2 to Dn represent data signals supplied to the data lines 102. FIGS. 5 and 6, respectively, show control by application of a first voltage and of a second voltage, respectively. FIGS. 7A to 7C are diagrams schematically showing gradation changes observed when visually recognized from a surface side of the device where the common electrode 110 shared across the electrophoretic elements 105 is arranged, and correspond to the timing charts of FIGS. 5 and 6. Specifically, FIGS. 7A to 7C schematically show gradation levels of respective pixels when a display status is changed from black to white through three times of scanning.

First, as shown in FIG. 5, potentials of the scan signals S1, S2 to Sm supplied to the respective scan lines 101 from the scan driver 130 are all set to high (selected status), thereby turning on the transistors 103 connected to the respective scan lines 101. In addition, at the same time, potentials of data signals D1, D2 to Dn output from the data driver 140 and input to the transistors 103 via the data lines 102 are all set to low. Thereby, the first voltage is applied to allow a potential of the common electrode 110 (the reference potential) to be higher than a potential supplied to each pixel electrode 111 (a low potential), thus enabling the black particles 113 to be distributed near the common electrode 110.

Next, as shown in FIG. 6, the potentials of the scan signals S1, S2 to Sm supplied to the respective scan lines 101 from the scan driver 130 are sequentially set to a high level (selected status), thereby sequentially turning on the transistors 103 connected to the scan lines 101. Then, the data signals D1, D2 to Dn output from the data driver 140 are supplied to the transistors 103 via the data lines 102 and input to the pixel electrodes 111. For example, the electrophoretic element 105 of the pixel 100 arranged in a second row and a second column receives the scan signal S2 and the data signal D2. In an example of FIG. 6, when the scan signal S2 is at a high potential (selected status) in a first scanning and a second scanning, the data signal D2 is at a high potential. Then, in a third scanning, when the scan signal S2 is at a high potential, the data signal D2 is at a low potential. That is, during the three times of scanning, the electrophoretic element 105 receives a positive pulse voltage (a positive potential voltage) twice. This allows a certain number of the black particles 113 among those distributed near the common electrode 110 to be gradually moved near the pixel electrode 111. Then, the electrophoretic element 105 has a gradation level corresponding to light gray after completion of the three times of scanning. Similarly, in the each selected status, the data signal is set at high or low potential according to need, and thereby, the pulse-form second voltage is applied to each electrophoretic element 105 an arbitrary number of times (in a range from zero to three times) during the three times of scanning. Consequently, upon completion of the three times of scanning, four gradation levels can be expressed. Scanning can be performed an arbitrary number of times, and thus, may be performed more than three times, for example.

Figure 8:
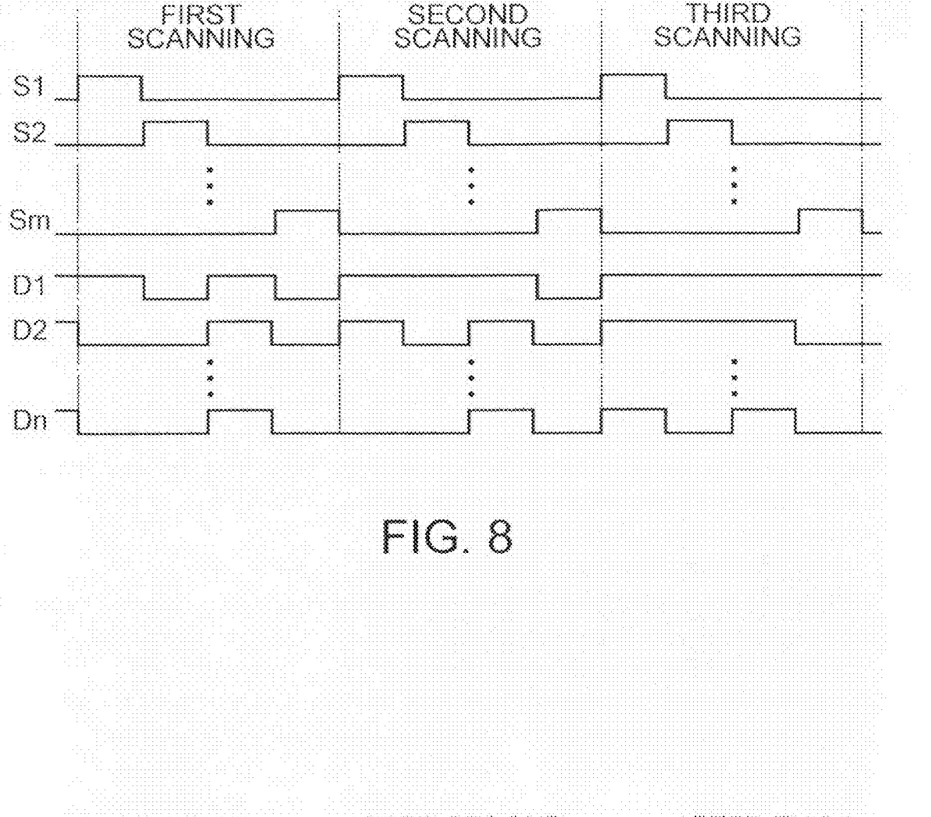
FIG. 8 is a timing chart illustrating another example of gradation control in the electrophoretic device.
Figure 9A:
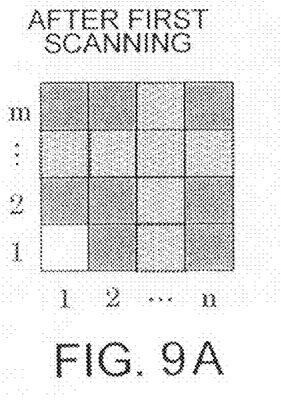
FIGS. 9A to 9C are diagrams schematically showing gradation changes in the electrophoretic element corresponding to the timing chart shown in FIG. 8.
Figure 9B:
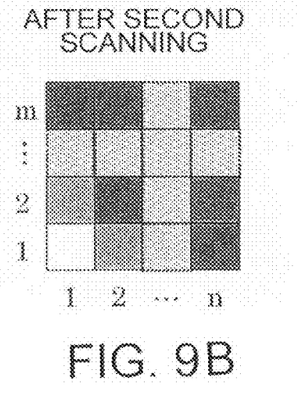
Figure 9C:
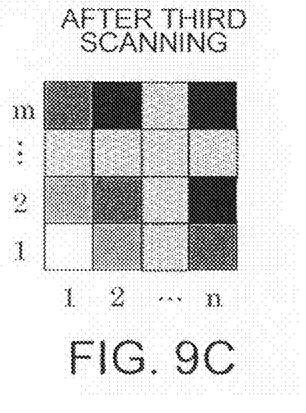

FIG. 8 is a timing chart illustrating another example of gradation control in the electrophoretic device. In the example of FIG. 8, the white particles 114 have a higher mobility than the black particles 113. The timing chart of FIG. 8 corresponds to the electrophoretic element 105 arranged at the m-th row and the n-th column in FIG. 1. Symbols S1, S2 to Sm represent the scan signals supplied to the respective scan lines 102, and symbols D1, D2 to Dn represent the data signals supplied to the respective data lines 102. FIGS. 9A to 9C are diagrams schematically showing gradation changes observed when visually recognized from the surface side where the common electrode 110 shared across the electrophoretic elements 105 is arranged, and correspond to the timing chart of FIG. 8. In addition, FIGS. 9A to 9C schematically show gradation levels of respective pixels in a display status change from white to black through three times of scanning.

First, similarly to the case of FIG. 5, the first voltage is applied. In FIG. 8, the data signals are all set to high potential to apply the first voltage such that the potential of the common electrode 110 (the reference potential) is lower than the potential supplied to the each pixel electrode 11, thereby allowing the white particles 114 to be distributed near the common electrode 110. Next, as shown in FIG. 8, the potentials of the scan signals S1, S2 to Sm supplied to the scan lines 101 from the scan driver 130 are sequentially set to high potential (selected status), thereby allowing the transistors 103 connected to the scan lines 101 to be sequentially turned on. Thereby, the data signals D1, D2 to Dn from the data driver 140 are supplied to the transistors 103 via the data lines 102 and input to the pixel electrodes 111. For example, the electrophoretic element 105 of the pixel 100 positioned in the second row and the second column receives the scan signal S2 and the data signal D2. In the example of FIG. 8, when the scan signal D2 is at a high potential (the selected status) in the first and the second scanning, the data signal D2 is at a low potential. Then, in the third scanning, when the scan signal S2 is at a high potential (the selected status), the data signal D2 is also at a high potential. That is, the electrophoretic element 105 receives a negative pulse voltage (a negative potential voltage) twice during the three times of scanning. Thereby, a part of the white particles 114 distributed near the common electrode 110 can be gradually moved near the pixel electrode 111. Consequently, the electrophoretic element 105 has a gradation level corresponding to dark gray after completion of the three times of scanning. Similarly, in the each selected status as above, the potential of the data signal is set to high or low according to need. Thereby, the pulse-form second voltage is applied to the electrophoretic element 105 an arbitrary number of times (in a range from zero to three times) during the three times of scanning. As a result, five gradation levels can be expressed by completing the three times of scanning. The number of times of scanning can be determined arbitrarily and may be more than three times.

Next, a detailed description will be given of mobilities of the black and the white electrophoretic particles and amounts of charge on the electrophoretic particles in the present embodiment.

The mobilities of the respective black and the white particles are expressed by a following equation (1):

$$u=(\epsilon_o\epsilon_r/\eta)\zeta \qquad (1)$$

In the above equation, symbol u represents an electrophoretic mobility (an electrophoretic velocity of the particle per electric field), symbol $\epsilon_o$ represents a vacuum permittivity, symbol $\epsilon_r$ represents a solvent relative permittivity, symbol $\eta$ represents a solvent viscosity, and symbol $\zeta$ represents a zeta potential. The equation (1) shows that the particle mobility is proportional to a charge amount (zeta potential) of each kind of the electrophoretic particles. For example, in the embodiment, the black and the white electrophoretic particles 113 and 114, respectively, have a charge amount (zeta potential) of −105 eV and of 37 eV, respectively. More strictly, it can be considered that the particle mobility depends, also, on a particle size. However, when generally-used electrophoretic particles are included in a same solvent, a diameter difference between the particles hardly influences the particles' mobilities. Thus, regardless of the diameter difference therebetween, the mobilities of the black and the white electrophoretic particles can be approximated as in the equation (1). In the embodiment, there is an approximately three-fold mobility difference between the black and the white particles 113 and 114, although an approximately two-fold difference may be set between the particles, for example.

Figure 10:
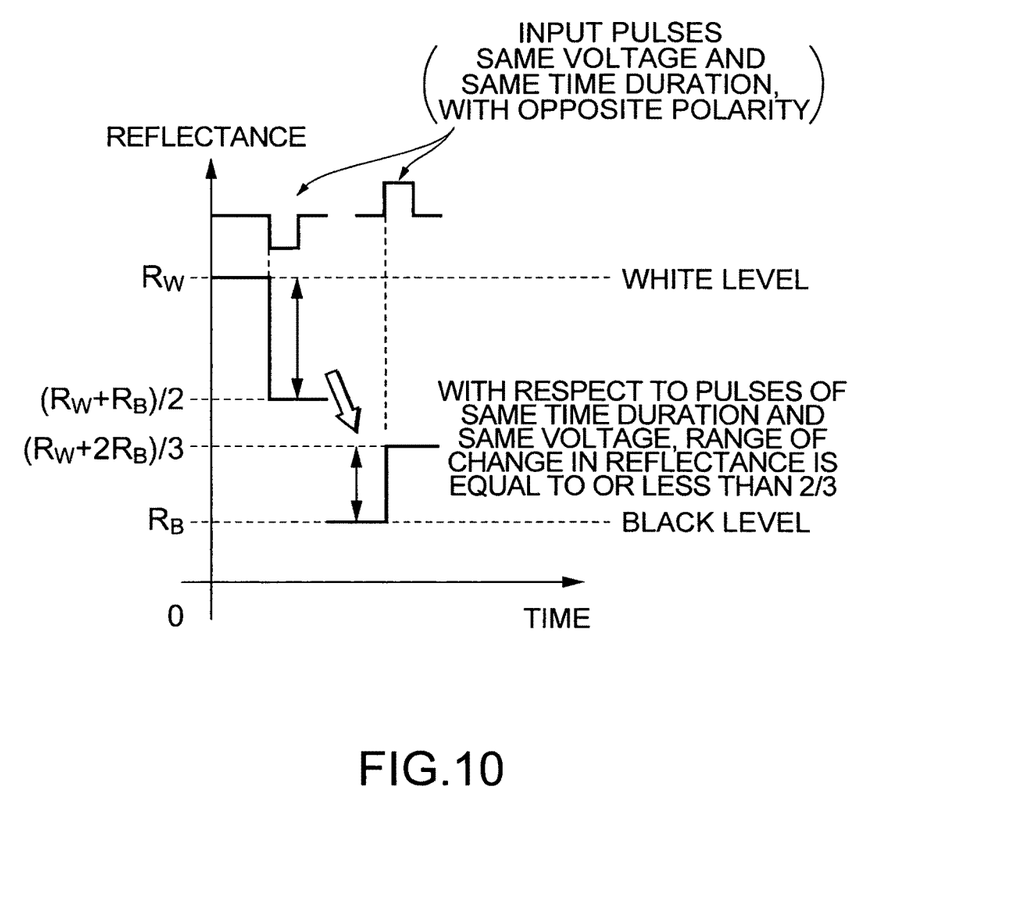
FIG. 10 is a diagram illustrating a method for indirectly determining a mobility difference by using a pixel reflectance as an index for estimating the mobility difference.

FIG. 10 illustrates a method for indirectly determining the mobility difference by using a pixel reflectance as an index for estimating the mobility difference. In FIG. 10, symbols $R_W$ and $R_B$, respectively, represent a reflectance in the white display status and a reflectance in the black display status, respectively, of the pixel 100. In addition, a time duration of a pulse and a voltage, respectively, at which the reflectance changes from $R_W$ to $R_W-(R_W-R_B)/2=(R_W+R_B)/2$ (a gray color at an exactly intermediate gradation level between white and black) are defined as T and V, respectively. In this case, it can be determined that a reflectance obtained when a pulse of −V is applied for the time duration T upon black display is equal to or less than $R_B+(R_W-R_B)/3-(R_W+2R_B)/3$. It is supposed that responses of the white particles are slower than those of the black particles (the mobility of the white particles is relatively low). That is, it means that a reflectance change obtained when a voltage is applied for the time duration T is equal to or less than ⅔ of a change rate obtained when a voltage of an opposite polarity is applied for the same time duration T. The coefficient of "⅔" is among many possible examples and the coefficient may be larger in a range up to approximately "¾".

Figure 11A:
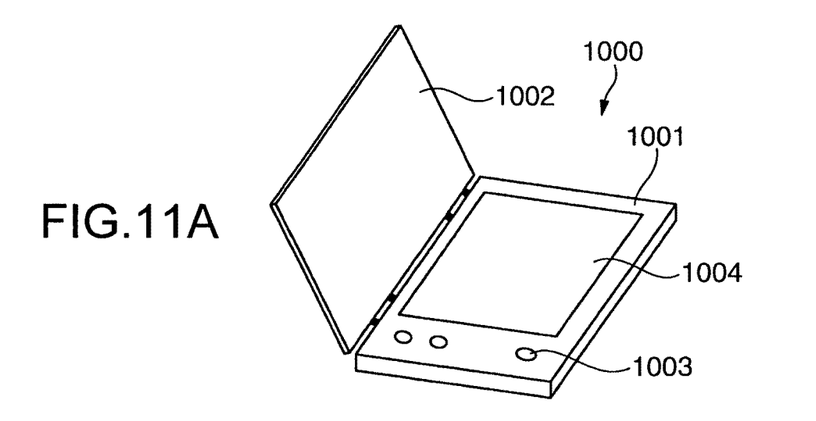
FIGS. 11A to 11C are perspective views of specific examples of an electronic apparatus applying the electrophoretic device.
Figure 11B:
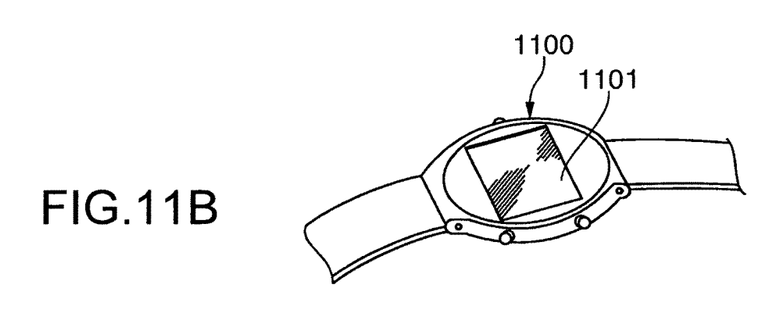
Figure 11C:
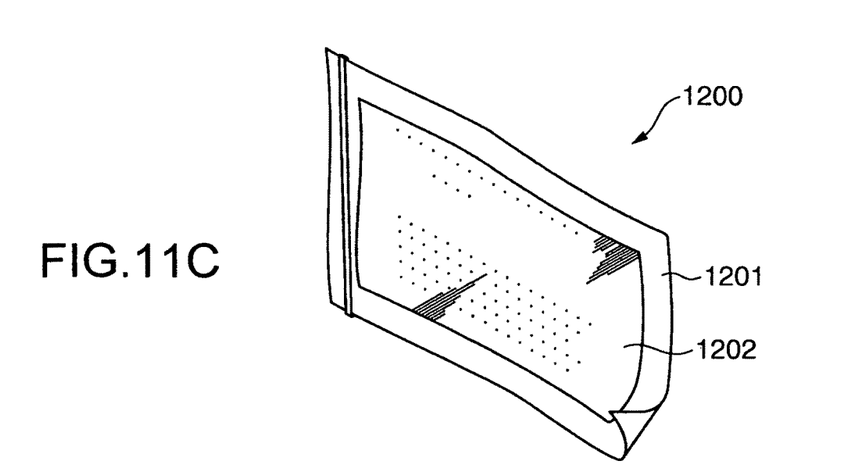

FIGS. 11A to 11C are perspective views illustrating specific examples of an electronic apparatus employing the electrophoretic device of the embodiment. FIG. 11A is a perspective view of an electronic book applied as an example of the electronic apparatus. An electronic book 1000 includes a book-shaped frame 1001, a (openable and closable) cover 1002 rotatably attached to the frame 1001, an operating section 1003, and a display 1004 formed by the electrophoretic device of the embodiment. FIG. 14B is a perspective view of a watch as another example of the electronic apparatus. An electronic watch 1100 includes a display 1101 formed by the electrophoretic device of the embodiment. FIG. 11C is a perspective view of an electronic paper as another example of the electronic apparatus. An electronic paper 1200 includes a main body 1201 formed by a rewritable sheet having a paper-like texture and flexibility and a display 1202 formed by the electrophoretic device of the embodiment. Examples of the electronic apparatus capable of applying the electrophoretic device of the embodiment are not restricted those above and include a wide range of apparatuses using visual tone changes associated with movement of the electrophoretic particles. For example, other than the electronic apparatuses as above, there may be mentioned products belonging to immobile objects such as a wall surface with an electrophoretic film provide thereon and to mobile objects such as vehicles, aircraft, and ships.

The embodiment described above uses the two kinds of the particles (the electrophoretic particles) having the different mobility provided in the electrophoretic layer. First, after performing the initial setting by applying the first voltage between the first and the second electrodes, the pulse-form second voltage is applied between the first and the second electrodes the plurality of number of times. The number of times of the voltage applications can provide the gradation control. This eliminates a need for high-precision pulse length control.

The invention is not restricted to the embodiment described above and can be practiced by making various modifications without departing from the spirit and the scope of the invention. For example, the embodiment described above is an example of the electrophoretic device formed as a so-called active-matrix display. However, the electrophoretic device of the embodiment can be applied similarly to an electrophoretic device formed as a segment display, or the like. In addition, the structure of the electrophoretic layer is not specifically restricted to that described above, and an electrophoretic layer having any structure such as a cell or a microcapsule may be used. In addition, in the above embodiment, the electrophoretic particles having high mobility are charged with negative electricity, whereas those having low mobility are charged with positive electricity. However, the charge condition may be vice versa. In that case, it is only necessary to reverse polarities of voltages applied between the common electrode and the pixel electrode with respect to the voltage polarities in the above embodiment.

Furthermore, while the embodiment described above considers easily performing high-precision gradation control, the electrophoretic device of the embodiment can be applied to an electrophoretic device using binary display that requires no gradation control. In order for such an electrophoretic device to immediately show dense display, it is more effective to use electrophoretic particles having higher mobility. To explain that in accordance with the above embodiment, all pixels are initially put in a white display status. Then, control is provided such that only necessary pixels are put in a black display status, thereby enabling a display speed to be accelerated as compared to vice versa. Accordingly, the electrophoretic device of the embodiment can be applied to both of electrophoretic devices for gradation display and to electrophoretic devices for binary display.

What is claimed is:

1. An electrophoretic device, comprising:
a first electrode, the first electrode being arranged on a display side of the electrophoretic device;
a second electrode;
an electrophoretic layer formed between the first electrode and the second electrode, the electrophoretic layer including:
a first particle charged with negative electricity and exhibiting a first color; and
a second particle charged with positive electricity, and exhibiting a second color; the first particle having a higher mobility than the second particle; and
a control circuit i) initially applying a first voltage between the first and the second electrodes such that the first electrode is at a higher potential than the second electrode so that the first particle moves towards the first electrode to correspond to a first color status; and ii) applying a plurality of pulse voltages between the first electrode and the second electrode such that the first electrode is at a lower potential than the second electrode, each of the pulse voltages having a substantially same voltage width and a second substantially same voltage value, the number of times of application of the pulse voltage being determined based on a desired gradation, wherein the voltage pulse width is smaller when shifting from the second color to the first color than when shifting from the first color to the second color.

2. The electrophoretic device according to claim 1, wherein the control unit supplies a reference potential to the first electrode and supplies a lower or higher potential than the reference potential to the second electrode to determine the first and the second voltages.

3. The electrophoretic device according to claim 1, wherein a display surface of the electrophoretic device is located on a side where the first electrode is arranged.

4. The electrophoretic device according to claim 1, wherein the first and the second voltages have an equal absolute value.

5. An electronic apparatus including the electrophoretic device according to claim 1.

6. A method for driving an electrophoretic device that includes: a plurality of first particles having a relatively high mobility, charged with negative electricity and exhibiting a first color and a plurality of second particles having a relatively low mobility, exhibiting a second color and charged with positive electricity in an electrophoretic layer; a first electrode and a second electrode to face each other via the electrophoretic layer; and a control unit to control a voltage applied between the first and the second electrodes, the method comprising:

(a) initially applying a first voltage between the first and the second electrodes by the control unit to control such that the first electrode is at a higher potential than the second electrode so as to allow the first particles to be distributed near the first electrode to correspond to a first color status; and (b) applying a pulse-form second voltage between the first and the second electrodes by the control unit intermittently a plurality of number of times to control such that the first electrode is at a lower potential than the second electrode so as to allow a part of the first particles distributed near the first electrode to move near the second electrode, each second voltage applied the plurality of number of times at step (b) having a substantially same pulse width and a substantially same voltage value, as well as the number of times of application of the second voltage being determined based on a desired gradation, wherein the voltage pulse width is smaller when shifting from the second color to the first color than when shifting from the first color to the second color.

7. The method for driving an electrophoretic device according to claim 6, wherein at step (a), the second particles are dispersed and distributed between the first and the second electrodes.

8. The method for driving an electrophoretic device according to claim 6, wherein the control unit supplies a reference potential to the first electrode and supplies a potential lower or higher than the reference potential to the second electrode to determine the first and the second voltages.

9. The method for driving an electrophoretic device according to claim 6, wherein the first and the second voltages have an equal absolute value.

10. An electrophoretic device, comprising:
a first electrode, the first electrode being arranged on a display side of the electrophoretic device;
a second electrode;
an electrophoretic layer formed between the first electrode and the second electrode, the electrophoretic layer including:
a first particle charged with positive electricity and exhibiting a first color; and
a second particle charged with negative electricity, and exhibiting a second color, the first particle having a higher mobility than the second particle; and
a control circuit i) initially applying a second voltage between the first and the second electrodes such that the first electrode is at a lower potential than the second electrode so that the first particle moves towards the first electrode to correspond to the first color status and ii) applying a plurality of pulse voltages between the first electrode and the second electrode such that the first electrode is at a higher potential than the second electrode, each of the pulse voltages having a second substantially same voltage width and a substantially same voltage value, the number of times of application of the pulse voltage being determined based on a desired gradation, wherein the voltage pulse width is smaller when shifting from the second color to the first color than when shifting from the first color to the second color.

* * * * *